United States Patent
Aoshima et al.

(10) Patent No.: US 10,624,831 B2
(45) Date of Patent: Apr. 21, 2020

(54) COSMETIC

(71) Applicants: OSAKA ORGANIC CHEMICAL INDUSTRY LTD., Azuchi-machi, Chuo-ku, Osaka (JP); SHISEIDO COMPANY, LTD., Chuo-ku, Tokyo (JP)

(72) Inventors: Hideyuki Aoshima, Hakusan (JP); Daisuke Iitsuka, Osaka (JP); Takumi Watanabe, Yokohama (JP); Kazuyuki Miyazawa, Yokohama (JP)

(73) Assignees: OSAKA ORGANIC CHEMICAL INDUSTRY LTD., Osaka (JP); SHISEIDO COMPANY, LTD., Tokyo (JP)

(*) Notice: Subject to any disclaimer, the term of this patent is extended or adjusted under 35 U.S.C. 154(b) by 0 days.

(21) Appl. No.: 15/553,620

(22) PCT Filed: Feb. 2, 2016

(86) PCT No.: PCT/JP2016/052978
§ 371 (c)(1),
(2) Date: Aug. 25, 2017

(87) PCT Pub. No.: WO2016/136398
PCT Pub. Date: Sep. 1, 2016

(65) Prior Publication Data
US 2018/0028430 A1 Feb. 1, 2018

(30) Foreign Application Priority Data
Feb. 28, 2015 (JP) ................................ 2015-039685

(51) Int. Cl.
| | | |
|---|---|---|
| *A61K 8/00* | (2006.01) | |
| *A61K 8/81* | (2006.01) | |
| *A61Q 1/02* | (2006.01) | |
| *A61K 8/91* | (2006.01) | |
| *A61Q 17/04* | (2006.01) | |
| *A61Q 1/10* | (2006.01) | |
| *A61Q 5/06* | (2006.01) | |
| *A61Q 19/00* | (2006.01) | |
| *C08F 220/18* | (2006.01) | |

(52) U.S. Cl.
CPC .............. *A61K 8/8152* (2013.01); *A61K 8/81* (2013.01); *A61K 8/8123* (2013.01); *A61K 8/91* (2013.01); *A61Q 1/02* (2013.01); *A61Q 1/10* (2013.01); *A61Q 5/06* (2013.01); *A61Q 17/04* (2013.01); *A61Q 19/00* (2013.01); *C08F 220/18* (2013.01); *A61K 2800/10* (2013.01); *C08F 2220/1858* (2013.01)

(58) Field of Classification Search
CPC .......... A61K 8/8152; A61K 8/81; A61K 8/91; A61K 8/8123; A61Q 1/02; A61Q 1/10; A61Q 5/06; A61Q 17/04; A61Q 19/00
See application file for complete search history.

(56) References Cited

U.S. PATENT DOCUMENTS

| | | | | |
|---|---|---|---|---|
| 5,965,656 | A | 10/1999 | Yamamoto et al. | |
| 2008/0262181 | A1* | 10/2008 | Kitano | C08F 220/18 526/312 |

FOREIGN PATENT DOCUMENTS

| | | |
|---|---|---|
| JP | 11-255995 | 9/1999 |
| JP | 2002-201110 | 7/2002 |
| JP | 2003-231609 | 8/2003 |
| JP | 2005-232279 | 9/2005 |
| JP | 2013-523899 | 6/2013 |

OTHER PUBLICATIONS

PCT/JP2016/052978 International Search Report and Written Opinion, dated May 10, 2016, 5 pages—English, 6 pages—Japanese.
Masamichi Morita et al., "Properties of the Perfluoroalkylethyl Acrylate (FA) Copolmers and Their Applications for Cosmetics", J. Soc. Cosmet. Chem. Jpn., 1999, vol. 33, No. 4, pp. 343-353, ISSN 03875253, 18844146.
Methacryloyl Ethylbetaine/ Acrylates Copolymer, Osaka Organic Chemical Industry Ltd., 2 pages, RAM Resin Series, printed May 10, 2019, http://www.ooc.co.jp/en/products/function/cosmetic_materials/betaine/.

* cited by examiner

*Primary Examiner* — Michael L Leonard
(74) *Attorney, Agent, or Firm* — Andrew F. Young, Esq.; Lackenbach Siegel, LLP

(57) ABSTRACT

A cosmetic is characterized by containing a polymer which is produced by polymerizing a fluorine atom-containing monomer represented by formula (I) (wherein $R^1$ represents a hydrogen atom or a methyl group; $R^2$ represents a hydrogen atom or a fluorine atom; m is an integer of 0 or 1 to 4; and n is an integer of 1 to 12), (B) a betaine monomer represented by formula (II) (wherein $R^3$ represents a hydrogen atom or a methyl group; $R^4$ and $R^5$ independently represent a hydrogen atom or an alkyl group having 1 to 4 carbon atoms; p represents an integer of 1 to 4: and q represents an integer of 1 to 4) and (C) a monomer component containing an alkyl (meth)acrylate represented by formula (III) (wherein $R^6$ represents a hydrogen atom or a methyl group and $R^7$ represents an alkyl group having 8 to 22 carbon atoms) with one another.

3 Claims, No Drawings

COSMETIC

CROSS REFERENCE TO RELATED APPLICATIONS

This application relates to and claims priority as a § 371 national phase, from PCT/JP2016/052978 filed Feb. 2, 2016, the entire contents of which are incorporated herein by reference, which in turn claims priority from JP 2015-039685 filed Feb. 28, 2015.

TECHNICAL FIELD

The present invention relates to a cosmetic. More specifically, the present invention relates to a cosmetic having both water repellency and oil repellency, and being excellent in water resistance and sebum resistance.

BACKGROUND ART

In cosmetics, particularly makeup cosmetics, it has been desired to prevent color dullness with the passage of time and to improve durability of an applied cosmetic. In sunscreen cosmetics, it has been desired to improve durability of an applied cosmetic. In hairstyling cosmetics, it has been desired to improve setting durability. In order to impart these properties to cosmetics, it is necessary to impart water repellency, oil repellency and secondary adhesion-preventing function to cosmetics.

In order to impart water repellency, oil repellency and secondary adhesion-preventing function to cosmetics, it has hitherto been studied that water resistance is improved by increasing a content of an oil component in cosmetics, that oil resistance is improved by lowering a content of an oil component in cosmetics, and that hydrophobizing treatment is carried out to a pigment which is to be used in cosmetics (see, for example, Patent Document 1).

However, all of the above-mentioned cosmetics are not only insufficient in effects on preventing color dullness with the passage of time or effects on durability of an applied cosmetic, but also do not have both water resistance and oil resistance. In recent years, therefore, it has been desired to develop a cosmetic having both water repellency and oil repellency, and being excellent in water resistance and sebum resistance.

PRIOR ART DOCUMENTS

Patent Document

Patent Document 1: JP 2005-232279 A

SUMMARY OF THE INVENTION

Problem to be Solved by the Invention

The present invention has been accomplished in view of the above-mentioned prior art. An object of the present invention is to provide a cosmetic having both water repellency and oil repellency, and being excellent in water resistance and sebum resistance.

Means for Solving the Problem

The present invention relates to
(1) a cosmetic including a polymer formed by a polymerization of a monomer component including (A) a fluorine atom-containing monomer represented by the formula (I):

[Chem. 1]

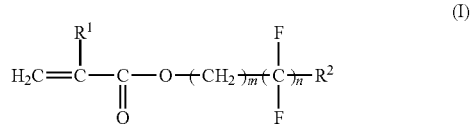

wherein $R^1$ is hydrogen atom or methyl group, $R^2$ is hydrogen atom or fluorine atom, m is 0 or an integer of 1 to 4, and n is an integer of 1 to 12; (B) a betaine monomer represented by the formula (II):

[Chem. 2]

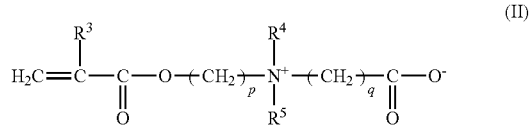

wherein $R^3$ is hydrogen atom or methyl group, each of $R^4$ and $R^5$ is independently hydrogen atom or an alkyl group having 1 to 4 carbon atoms, p is an integer of 1 to 4, and q is an integer of 1 to 4; and (C) an alkyl (meth)acrylate represented by the formula (III):

[Chem. 3]

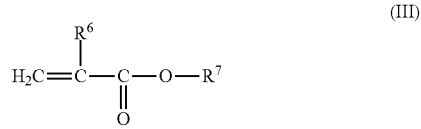

wherein $R^6$ is hydrogen atom or methyl group, and $R^7$ is an alkyl group having 8 to 22 carbon atoms;
(2) the cosmetic according to the above-mentioned item (1), wherein the monomer component further includes a monomer having a sulfonic acid group or a sulfonate group;
(3) the cosmetic according to the above-mentioned item (1) or (2), wherein the monomer component further includes a cross-linking agent represented by the formula (IV):

[Chem. 4]

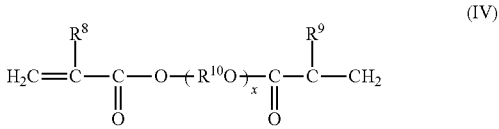

wherein each of $R^8$ and $R^9$ is independently hydrogen atom or methyl group, $R^{10}$ is an alkylene group having 2 or 3 carbon atoms, and r is an integer of 1 to 40.

In the present invention, the term "(meth)acrylate" means "acrylate" or "methacrylate".

Effect of the Invention

According to the present invention, there is provided a cosmetic having both water repellency and oil repellency, and being excellent in water resistance and sebum resistance.

MODES FOR CARRYING OUT THE INVENTION

As described above, the cosmetic of the present invention is characterized in that the cosmetic includes a polymer formed by a polymerization of a monomer component including (A) a fluorine atom-containing monomer represented by the formula (I):

[Chem. 5]

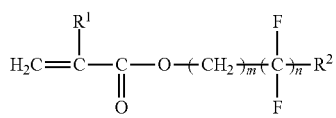
(I)

wherein $R^1$ is hydrogen atom or methyl group, $R^2$ is hydrogen atom or fluorine atom, m is 0 or an integer of 1 to 4, and n is an integer of 1 to 12; (B) a betaine monomer represented by the formula (II):

[Chem. 6]

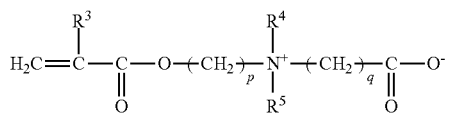
(II)

wherein $R^3$ is hydrogen atom or methyl group, each of $R^4$ and $R^5$ is independently hydrogen atom or an alkyl group having 1 to 4 carbon atoms, p is an integer of 1 to 4, and q is an integer of 1 to 4; and (C) an alkyl (meth)acrylate represented by the formula (III):

[Chem. 7]

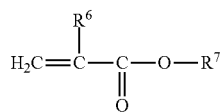
(III)

wherein $R^6$ is hydrogen atom or methyl group, and $R^7$ is an alkyl group having 8 to 22 carbon atoms.

In the fluorine atom-containing monomer represented by the formula (I), $R^1$ is hydrogen atom or methyl group, $R^2$ is hydrogen atom or fluorine atom, m is 0 or an integer of 1 to 4, and n is an integer of 1 to 12.

Although m is 0 or an integer of 1 to 4, m is preferably an integer of 1 to 4, and more preferably an integer of 2 to 4, from the viewpoint of impartment of water repellency and oil repellency and improvement in water resistance and sebum resistance. Although n is an integer of 1 to 12, n is preferably an integer of 2 to 10 and more preferably an integer of 4 to 8, from the viewpoint of impartment of water repellency and oil repellency and improvement in water resistance and sebum resistance.

The fluorine atom-containing monomer represented by the formula (I) includes, for example, 2-perfluorohexyl-2-ethyl acrylate and the like, and the present invention is not limited only to those exemplified ones. The fluorine atom-containing monomer represented by the formula (I) can be easily commercially obtained. Examples of the fluorine atom-containing monomer include, for example, a fluorine atom-containing monomer having the formula (I) in which $R^1$ is hydrogen atom, $R^2$ is fluorine atom, m is 2, and n is 6 [for example, trade name: Viscoat 13F manufactured by Osaka Organic Chemical Industry Ltd., and the like], a fluorine atom-containing monomer having the formula (I) in which $R^1$ is hydrogen atom, $R^2$ is hydrogen atom, m is 1, and n is 1 [for example, trade name: Viscoat 4F manufactured by Osaka Organic Chemical Industry Ltd., and the like], a fluorine atom-containing monomer having the formula (I) in which $R^1$ is methyl group, $R^2$ is hydrogen atom, m is 1, and n is 3 [for example, trade name: Viscoat 8FM manufactured by Osaka Organic Chemical Industry Ltd., and the like], and the like The present invention is not limited only to those exemplified ones.

The content of the fluorine atom-containing monomer represented by the formula (I) in the monomer component is preferably 1 to 30% by mass, more preferably 1 to 25% by mass, and further preferably 2 to 20% by mass, from the viewpoint of impartment of water repellency and oil repellency to the cosmetic, and improvement in water resistance and sebum resistance.

In the betaine monomer represented by the formula (II), $R^3$ is hydrogen atom or methyl group, each of $R^4$ and $R^5$ is independently hydrogen atom or an alkyl group having 1 to 4 carbon atoms, p is an integer of 1 to 4, and q is an integer of 1 to 4.

The betaine monomer represented by the formula (II) includes, for example, N-(meth)acryloyloxymethyl-N,N-dimethylammonium-α-N-methylcarboxybetaine, N-(meth)acryloyloxyethyl-N,N-dimethylammonium-α-N-methylcarboxybetaine, N-(meth)acryloyloxypropyl-N,N-dimethylammonium-α-N-methylcarboxybetaine, N-(meth)acryloyloxymethyl-N,N-diethylammonium-α-N-methylcarboxybetaine, N-(meth)acryloyloxyethyl-N,N-diethylammonium-α-N-methylcarboxybetaine, N-(meth)acryloyloxypropyl-N,N-diethylammonium-α-N-methylcarboxybetaine, and the like. The present invention is not limited only to those exemplified ones. These betaine monomers can be used alone or in combination of at least two kinds thereof.

The betaine monomer represented by the formula (II) can be easily prepared, for example, by methods as described in JP Hei 9-95474 A, JP Hei 9-95586 A, JP Hei 11-222470 A and the like.

The betaine monomer represented by the formula (II) can be easily commercially obtained under the trade name of, for example, GLBT manufactured by Osaka Organic Chemical Industry Ltd., and the like.

Among the betaine monomers represented by the formula (II), N-methacryloyloxyethyl-N, N-dimethylammonium-α-N-methylcarboxybetaine is preferred from the viewpoint of impartment of water repellency and oil repellency and improvement in water resistance and sebum resistance.

The content of the betaine monomer represented by the formula (II) in the monomer component is preferably 3 to 80% by mass, more preferably 3 to 75% by mass, and further preferably 5 to 70% by mass, from the viewpoint of impartment of water repellency and oil repellency and improvement in water resistance and sebum resistance.

In the alkyl (meth)acrylate represented by the formula (III), $R^6$ is hydrogen atom or methyl group, and $R^7$ is an alkyl group having 8 to 22 carbon atoms.

The alkyl (meth)acrylate represented by the formula (III) includes, for example, alkyl (meth)acrylates having an alkyl group with 8 to 22 carbon atoms, each of alkyl (meth)acrylates constituting an ester, such as 2-ethylhexyl (meth)acrylate, n-octyl (meth)acrylate, isooctyl (meth)acrylate, n-nonyl (meth)acrylate, isononyl (meth)acrylate, 2-ethylhexyl (meth)acrylate, decyl (meth)acrylate, lauryl (meth)acrylate, tridecyl (meth)acrylate, tetradecyl (meth)acrylate, hexadecyl (meth)acrylate, octadecyl (meth)acrylate, isostearyl (meth)acrylate, eicosyl (meth)acrylate, and the like. The present invention is not limited only to those exemplified ones. These alkyl (meth)acrylates can be used alone or in combination of at least two kinds thereof.

The content of the alkyl (meth)acrylate represented by the formula (III) in the monomer component is preferably 10 to 80% by mass, more preferably 15 to 75% by mass, and further preferably 20 to 70% by mass, from the viewpoint of impartment of water repellency and oil repellency and improvement in water resistance and sebum resistance.

It is preferred that the monomer component contains a monomer having a sulfonic acid group or a sulfonate group in its molecule from the viewpoint of improvement in oil repellency.

The monomer having a sulfonic acid group includes, for example, sodium acryloyldimethyltaurine, sodium methacryloyldimethyltaurine, 2-acrylamide-2-methylpropanesulfonic acid, 2-methacrylamide-2-methylpropanesulfonic acid, 2-acrylamide-2-ethylpropanesulfonic acid, 2-methacrylamide-2-ethylpropanesulfonic acid, 2-acrylamide-2-propylpropanesulfonic acid, 2-methacrylamide-2-propylpropanesulfonic acid, and the like. The present invention is not limited only to those exemplified ones. These sulfonic acid group-containing monomers can be used alone or in combination of at least two kinds thereof.

The monomer having a sulfonate group is preferred from the viewpoint of improving oil repellency. The sulfonate group of the monomer having a sulfonate group can be formed, for example, by neutralizing the sulfonic acid group-containing monomer with a neutralizer such as triethanolamine. The neutralization of the sulfonic acid group of the sulfonic acid group-containing monomer can be carried out to the sulfonic acid group-containing monomer or a polymer obtained by polymerizing the monomer component.

The content of the monomer having a sulfonic acid group or a sulfonate group in the monomer component is preferably 0% by mass or more, more preferably 1% by mass or more, further preferably 3% by mass or more, and still further preferably 5% by mass or more, from the viewpoint of improvement in oil repellency. The content of the monomer having a sulfonic acid group or a sulfonate group in the monomer component is preferably 40% by mass or less, more preferably 35% by mass or less, and further preferably 30% by mass or less, from the viewpoint of improvement in water repellency.

The monomer component can contain other monomers so far as an object of the present invention is not hindered.

The other monomers includes, for example, monofunctional monomers such as aliphatic monocarboxylic acids such as acrylic acid, methacrylic acid, itaconic acid and maleic anhydride; hydroxyalkyl (meth)acrylates such as 2-hydroxyethyl acrylate, 2-hydroxyethyl methacrylate, hydroxypropyl acrylate, hydroxypropyl methacrylate, hydroxybutyl acrylate and hydroxybutyl methacrylate; cycloalkyl (meth)acrylates such as cyclohexyl acrylate and cyclohexyl methacrylate; aryl (meth)acrylates such as benzyl acrylate and benzyl methacrylate; alkoxyalkyl (meth)acrylates such as methoxyethyl acrylate, methoxyethyl methacrylate, methoxybutyl acrylate and methoxybutyl methacrylate; alkyl carbitol (meth)acrylates such as ethyl carbitol acrylate and ethyl carbitol methacrylate; alkyl (meth)acrylamides such as N-methylacrylamide, N-methyl methacrylamide, N-ethyl acrylamide, N-ethyl methacrylamide, N-propyl acrylamide, N-propyl methacrylamide, N-isopropyl acrylamide, N-isopropyl methacrylamide, N-tert-butyl acrylamide, N-tert-butyl methacrylamide, N-octyl acrylamide, N-octyl methacrylamide, N,N-dimethylacrylamide, N,N-dimethyl methacrylamide, N,N-diethyl acrylamide and N,N-diethyl methacrylamide; alkoxy (meth)acrylamides such as N-butoxy methylacrylamide and N-butoxy methyl methacrylamide; (meth)acryloyl morpholines such as acryloyl morpholine and methacryloyl morpholine; diacetone (meth)acrylamides such as diacetone acrylamide and diacetone methacrylamide; styrene-based monomers such as styrene and methylstyrene; fatty acid alkyl esters having an alkyl group with 1 to 4 carbon atoms other than (meth)acrylic acid alkyl ester, such as methyl itaconate and ethyl itaconate; fatty acid vinyl esters such as vinyl acetate and vinyl propionate; nitrogen atom-containing monomers such as N-vinylpyrrolidone and N-vinylcaprolactam, and the like. The present invention is not limited only to those exemplified ones. These other monomers can be used alone or in combination of at least two kinds thereof.

From the viewpoint of impartment of water repellency and oil repellency and improvement in water resistance and sebum resistance, it is preferred that the monomer component contains a cross-linking agent represented by the formula (IV):

[Chem. 8]

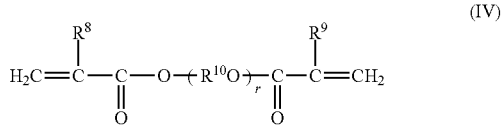

wherein each of $R^8$ and $R^9$ is independently hydrogen atom or methyl group, $R^{10}$ is an alkylene group having 2 or 3 carbon atoms, and r is an integer of 1 to 40.

In the formula (IV), each of $R^8$ and $R^9$ is independently hydrogen atom or methyl group, $R^{10}$ is an alkylene group having 2 or 3 carbon atoms, and r is an integer of 1 to 40. From the viewpoint of impartment of water repellency and oil repellency and improvement in water resistance and sebum resistance, r is preferably an integer of 1 to 20, and more preferably an integer of 2 to 18.

The cross-linking agent represented by the formula (IV) includes, for example, (poly)ethylene glycol di(meth)acrylates such as ethylene glycol diacrylate, ethylene glycol dimethacrylate, diethylene glycol diacrylate, diethylene glycol dimethacrylate, triethylene glycol diacrylate, triethylene glycol dimethacrylate, tetraethylene glycol diacrylate, tetraethylene glycol dimethacrylate, polyethylene glycol diacrylate other than the above-mentioned ones, and polyethylene glycol dimethacrylate other than the above-mentioned ones; (poly)propylene glycol di(meth)acrylates such as propylene glycol diacrylate, propylene glycol dimethacrylate, dipropylene glycol diacrylate, dipropylene glycol dimethacrylate, tripropylene glycol diacrylate, tripropylene glycol dimethacrylate, tetrapropylene glycol diacrylate, tetrapropylene glycol dimethacrylate, polypropylene glycol diacrylate other than the above-mentioned ones, and polypropylene glycol dimethacrylate other than the above-mentioned ones, and the like. The present invention is not limited only to those exemplified ones. These cross-linking agents can be used alone or in combination of at least two kinds thereof.

The content of the cross-linking agent in the monomer component is preferably 0.3 to 15% by mass, more preferably 0.5 to 15% by mass, and further preferably 1 to 10% by mass, from the viewpoint of improvement in water repellency, oil repellency and durability of oil repellency, and from the viewpoints of impartment of water repellency and oil repellency and improvement in water resistance and sebum resistance.

When the monomer component is polymerized, a chain transfer agent can be used for adjusting a molecular weight of a resulting polymer. The chain transfer agent includes, for example, compounds having a mercaptan group, such as lauryl mercaptan, dodecyl mercaptan and thioglycerol, inorganic salts such as sodium hypophosphite and sodium bisulfate, and the Like. The present invention is not limited only to those exemplified ones. The amount of the chain transfer agent per 100 parts by mass of the monomer component is preferably 0.01 to 10 parts by mass or so.

The polymerization of the monomer component can be carried out, for example, by a method such as a homogeneous solution polymerization method, a heterogeneous solution polymerization method, an emulsion polymerization method, an inverse emulsion polymerization method, a bulk polymerization method, a suspension polymerization method or a precipitation polymerization method.

When the monomer component is polymerized by a solution polymerization method, a solvent is used. The solvent includes, for example, alcohol-based solvents such as methanol, ethanol, propyl alcohol, isopropyl alcohol and butyl alcohol; hydrocarbon-based solvents such as hexane, heptane, octane, isooctane, decane and liquid paraffin; ether-based solvents such as dimethyl ether, diethyl ether and tetrahydrofuran; ketone-based solvents such as acetone and methyl ethyl ketone; ester-based solvents such as methyl acetate, ethyl acetate and butyl acetate; chloride-based solvents such as methylene chloride, chloroform and carbon tetrachloride; dimethylformamide, diethylformamide, dimethylsulfoxide, dioxane, and the like. The present invention is not limited only to those exemplified ones. These solvents can be used alone or in combination of at least two kinds thereof. The amount of the solvent cannot be absolutely determined since the amount differs depending upon kinds of the solvent. It is preferred that the amount of the solvent is usually 100 to 1000 parts by mass or so per 100 parts by mass of the monomer component.

When the monomer component is polymerized, a polymerization initiator can be used. The polymerization initiator includes, for example, a thermal polymerization initiator, a photopolymerization initiator, and the like.

The thermal polymerization initiator includes, for example, azo-based polymerization initiators such as dimethyl-2,2'-azobis(2-methylpropionate), azoisobutyronitrile, methyl azoisobutyrate and azobisdimethylvaleronitrile; peroxide-based polymerization initiators such as benzoyl peroxide, potassium persulfate and ammonium persulfate, and the like. The present invention is not limited only to those exemplified ones. These polymerization initiators can be used alone or in combination of at least two kinds thereof.

The photopolymerization initiator includes, for example, 2-oxoglutaric acid, 1-hydroxycyclohexyl phenyl ketone, 2-hydroxy-2-methyl-1-phenylpropan-1-one, 2-methyl [4-(methylthio)phenyl]-2-morpholinopropan-1-one, 2,2-dimethoxy-1,2-diphenylethan-1-one, benzophenone, 1-[4-(2-hydroxyethoxy)phenyl]-2-hydroxy-2-methyl-1-propan-1-one, 2-benzyl-2-dimethylamino-1-(4-morpholinophenyl)butan-1-one, bis(2,6-dimethoxybenzoyl)-2,4,4-trimethylpentylphosphine oxide, and the like. The present invention is not limited only to those exemplified ones. These polymerization initiators can be used alone or in combination of at least two kinds thereof.

The amount of the polymerization initiator cannot be absolutely determined since the amount differs depending upon, for example, kinds of the polymerization initiator, and the like. It is preferred that the amount of the polymerization initiator is usually 0.01 to 10 parts by mass or so per 100 parts by mass of the monomer component.

When the monomer component is polymerized, its atmosphere is not particularly limited. The atmosphere can be the air or an inert gas such as nitrogen gas or argon gas.

The polymerization temperature of the monomer component is not particularly limited. It is preferred that the polymerization temperature of the monomer component is usually a temperature of 5 to 80° C. or so. The period of time necessary for the polymerization of the monomer component cannot be absolutely determined since the period of time for the polymerization differs depending upon conditions of the polymerization. Therefore, the period of time for the polymerization is arbitrary. The polymerization reaction can be arbitrarily terminated at the time when the amount of the remaining monomer becomes 10% by mass or less. The amount of the remaining monomer can be determined, for example, by adding bromine to the double bond of the monomer, and measuring the content of a double bond.

A polymer is obtained by carrying out a polymerization of the monomer component in a manner as mentioned above. The weight-average molecular weight of the polymer is not particularly limited. It is preferred that the weight-average molecular weight of the polymer is usually 3000 to 100000 or so. The weight-average molecular weight of the polymer is a value as determined by gel permeation chromatography (GPC). When the cross-linking agent is contained in the monomer component, it is difficult to determine a weight-average molecular weight of a resulting polymer because the polymer has a cross-linking structure.

The above-mentioned polymer can be neutralized as mentioned above as occasion demands. A neutralizer includes, for example, triethanolamine, dimethyl ethanol amine, diethyl ethanol amine, morpholine, ammonia water, sodium hydroxide and the like, and the present invention is not limited only to those exemplified ones. These neutralizers can be used alone or in combination of at least two kinds thereof.

The above-mentioned polymer can be used as it is according to its use and the like. The polymer can be purified, for example, by a purification method such as distillation or extraction as occasion demands in order to remove a solvent, an unreacted monomer and the like.

The cosmetic of the present invention is characterized in that the cosmetic contains the above-mentioned polymer. The cosmetic of the present invention can be prepared by including the above-mentioned polymer in the formulation of the cosmetic. The content of the above-mentioned polymer in the cosmetic of the present invention is preferably 1 to 95% by mass, and more preferably 5 to 95% by mass, from the viewpoint of preparation of a cosmetic having a desired formulation, impartment of water repellency and oil repellency, and improvement in water resistance and sebum resistance.

The cosmetic of the present invention can contain components which are generally used for cosmetics, such as water, oil, a surfactant, a thickener, a preservative, a perfume, a UV absorber, a moisturizer, a physiologically active component, a salt, an antioxidant, a chelating agent, a neutralizer and a pH adjusting agent other than the above-mentioned polymer, as long as effects of the present invention are not hindered.

The cosmetic of the present invention obtained as described in the above has water repellency and oil repellency, and is excellent in water resistance and sebum resistance. Thus, the cosmetic of the present invention can be suitably used for various cosmetics.

The form of the cosmetic of the present invention includes, for example, makeup cosmetics such as foundation, foundation primer, face finishing powder, rouge, eye shadow, cheek color, mascara and eyeliner, sunscreen, sunscreen cream, base cream, hair cream, emulsion, gel, mascara, hair spray, hair wax, an overcoat agent, and the like. The present invention is not limited only to those exemplified ones.

EXAMPLES

Next, the present invention will be more specifically described in accordance with working examples, and the present invention is not limited only to those examples.

Synthetic Example 1

To a 500-mL five-neck flask equipped with a stirring device, an inert gas inlet, a reflux condenser and a thermometer were added 10 g of 2-perfluorohexyl-2-ethyl acrylate, 5 g of N-methacryloyloxyethyl-N,N-dimethylammonium-N-α-methylcarboxybetaine, 10 g of sodium acryloyldimethyltaurine, 70 g of 2-ethylhexyl acrylate, 5 g of tridecyl ethylene glycol dimethacrylate and 2,340 g of ethyl alcohol. The temperature of the contents in the flask was raised to 75° C., and then 0.6 g of dimethyl-2,2'-azobis(2-methylpropionate) [manufactured by Wako Pure Chemical Industries, Ltd. under a product number of V-601] was added to the flask. A polymerization reaction of the contents was carried out by refluxing with stirring for 8 hours, to give a polymer.

Synthetic Example 2

To a 500-mL five-neck flask equipped with a stirring device, an inert gas inlet, a reflux condenser and a thermometer were added 10 g of 2-perfluorohexyl-2-ethyl acrylate, 5 g of N-methacryloyloxyethyl-N,N-dimethylammonium-N-α-methylcarboxybetaine, 10 g of sodium acryloyldimethyltaurine, 70 g of 2-ethylhexyl acrylate, 5 g of tetraethylene glycol dimethacrylate and 234.0 g of ethyl alcohol. The temperature of the contents in the flask was raised to 75° C., and then 0.6 g of dimethyl-2,2'-azobis(2-methylpropionate) [manufactured by Wako Pure Chemical Industries, Ltd. under a product number of V-601] was added to the flask. A polymerization reaction of the contents was carried out by refluxing with stirring for 8 hours, to give a polymer.

Synthetic Example 3

To a 500-mL five-neck flask equipped with a stirring device, an inert gas inlet, a reflux condenser and a thermometer were added 10 g of 2-perfluorohexyl-2-ethyl acrylate, 5 g of N-methacryloyloxyethyl-N,N-dimethylammonium-N-α-methylcarboxybetaine, 10 g of sodium acryloyldimethyltaurine, 65 g of 2-ethylhexyl acrylate, 10 g of tripropylene glycol diacrylate and 2,340 g of ethyl alcohol. The temperature of the contents in the flask was raised to 75° C., and then 0.6 g of dimethyl-2,2'-azobis(2-methylpropionate) [manufactured by Wako Pure Chemical Industries, Ltd. under a product number of V-601] was added to the flask. A polymerization reaction of the contents was carried out by refluxing with stirring for 8 hours, to give a polymer.

Comparative Synthetic Example 1

To a 500-mL five-neck flask equipped with a stirring device, an inert gas inlet, a reflux condenser and a thermometer were added 20 g of N-methacryloyloxyethyl-N,N-dimethylammonium-N-α-methylcarboxybetaine, 80 g of 2-ethylhexyl acrylate and 234.0 g of ethyl alcohol. The temperature of the contents in the flask was raised to 75° C., and then 0.6 g of dimethyl-2,2'-azobis(2-methylpropionate) [manufactured by Wako Pure Chemical Industries, Ltd. under a product number of V-601] was added to the flask. A polymerization reaction of the contents was carried out by refluxing with stirring for 8 hours, to give a polymer.

Comparative Synthetic Example 2

To a 500-mL five-neck flask equipped with a stirring device, an inert gas inlet, a reflux condenser and a thermometer were added 10 g of 2-perfluorohexyl-2-ethyl acrylate, 90 g of 2-ethylhexyl acrylate and 2,340 g of ethyl alcohol. The temperature of the contents in the flask was raised to 75° C., and then 0.6 g of dimethyl-2,2'-azobis(2-methylpropionate) [manufactured by Wako Pure Chemical Industries, Ltd. under a product number of V-601] was added to the flask. A polymerization reaction of the contents was carried out by refluxing with stirring for 8 hours, to give a polymer.

Comparative Synthetic Example 3

To a 500-mL five-neck flask equipped with a stirring device, an inert gas inlet, a reflux condenser and a thermometer were added 20 g of 2-perfluorohexyl-2-ethyl acrylate, 80 g of N-methacryloyloxyethyl-N,N-dimethylammonium-N-α-methylcarboxybetaine and 234.0 g of ethyl alcohol. The temperature of the contents in the flask was raised to 75° C., and then 0.6 g of dimethyl-2,2'-azobis(2-methylpropionate) [manufactured by Wako Pure Chemical Industries, Ltd. under a product number of V-601] was added to the flask. A polymerization reaction of the contents was carried out by refluxing with stirring for 8 hours, to give a polymer.

Comparative Synthetic Example 4

To a 500-mL five-neck flask equipped with a stirring device, an inert gas inlet, a reflux condenser and a thermometer were added 10 g of 2-perfluorohexyl-2-ethyl acrylate, 20 g of N-methacryloyloxyethyl-N,N-dimethylammonium-N-α-methylcarboxybetaine, 70 g of butyl acrylate and 2340 g of ethyl alcohol. The temperature of the contents in the flask was raised to 75° C., and then 0.6 g of dimethyl-2,2'-azobis(2-methylpropionate) [manufactured by Wako Pure Chemical Industries, Ltd. under a product number of V-601] was added to the flask. A polymerization reaction of the contents was carried out by refluxing with stirring for 8 hours, to give a polymer.

Examples 1 to 5 and Comparative Examples 1 to 6

Components 1 to 6 as shown in Table 1 or Table 2 were mixed with each other, to give an aqueous phase. Next, components 7 to 15 as shown in Table 1 or Table 2 were added to the aqueous phase obtained in the above, to give a cosmetic. Incidentally, the component 7 was used as a solvent for the components 8 to 15.

Examples 6 to 10 and Comparative Examples 7 to 12

Components 1 to 7 as shown in Table 3 or Table 4 were mixed with each other, to give an aqueous phase. Next, components 8 to 16 as shown in Table 3 or Table 4 were added to the aqueous phase obtained in the above, and then an oil phase composed of components 17 to 22 was added to the aqueous phase. The resulting mixture was emulsified, to give a cosmetic. Incidentally, the component 8 was used as a solvent for the components 9 to 16.

Next, as physical properties of the cosmetics obtained in the above, contact angle, water resistance and sebum resistance were evaluated in accordance with the following methods. The results are described in each table.

[Contact Angle]

An ethanol solution of the cosmetic obtained in each Example or each Comparative Example (content of a polymer: 20% by mass) was applied onto a glass substrate by using a doctor blade, and the resulting film was sufficiently dried at room temperature.

Next, one droplet of water or liquid oil (macadamia nut oil) in an amount of 2 μL was dropped on the above-mentioned film. After one second passed from dropping, a contact angle of the droplet was measured by using a contact angle meter (manufactured by Kyowa Interface Science Co., Ltd. under a product number of DM-501).

[Water Resistance]

An area of 3 cm×3 cm of a forearm part was coated with 20 μL of the cosmetic obtained in each Example or each Comparative Example, and the cosmetic was uniformly spread thereon. Thereafter, the cosmetic was sufficiently dried at room temperature. When the area where the forearm part was coated with the cosmetic was washed with running water, condition of removal of each cosmetic was visually observed by 20 expert panelists, and water resistance was evaluated in accordance with the following criteria for evaluation.

(Criteria for Evaluation)

A: The number of persons who evaluated that the cosmetic is "not removed" or "difficult to remove" is 16 or more.
B: The number of persons who evaluated that the cosmetic is "not removed" or "difficult to remove" is 10 to 15.
C: The number of persons who evaluated that the cosmetic is "not removed" or "difficult to remove" is 9 or less.

[Sebum Resistance]

An area of 3 cm×3 cm of a forearm part was coated with 20 μL of the cosmetic obtained in each Example or each Comparative Example, and the cosmetic was uniformly spread thereon. Thereafter, the cosmetic was sufficiently dried at room temperature. The area where the forearm part was coated with the cosmetic was coated with liquid oil (macadamia nut oil) in an appropriate amount, and the liquid oil was fitted to the forearm part. When the liquid oil was wiped off with a paper towel, condition of removal of each cosmetic was visually observed by 20 expert panelists, and sebum resistance was evaluated in accordance with the following criteria for evaluation.

(Criteria for Evaluation)

A: The number of persons who evaluated that the cosmetic is "not removed" or "difficult to remove" is 16 or more.
B: The number of persons who evaluated that the cosmetic is "not removed" or "difficult to remove" is 10 to 15.
C: The number of persons who evaluated that the cosmetic is "not removed" or "difficult to remove" is 9 or less.

TABLE 1

| | Component (% by mass) | Example 1 | Example 2 | Example 3 | Example 4 | Example 5 |
|---|---|---|---|---|---|---|
| 1 | Purified water | Balance | Balance | Balance | Balance | Balance |
| 2 | Edetic acid trisodium | Appropriate amount | Appropriate amount | Appropriate amount | Appropriate amount | Appropriate amount |
| 3 | Glycerol | 5 | 5 | 5 | 5 | 5 |
| 4 | Dipropylene glycol | 5 | 5 | 5 | 5 | 5 |
| 5 | Phenoxyethanol | 0.5 | 0.5 | 0.5 | 0.5 | 0.5 |
| 6 | Carbomer | 0.4 | 0.4 | 0.4 | 0.4 | 0.4 |
| 7 | Ethanol | 12 | 12 | 12 | 6 | 5 |
| 8 | Polymer of Synthetic Example 1 | 3 | — | — | 1.5 | 1 |
| 9 | Polymer of Synthetic Example 2 | — | 3 | — | — | — |
| 10 | Polymer of Synthetic Example 3 | — | — | 3 | — | — |
| Physical property | Contact angle (°) with water | 133 | 124 | 124 | 119 | 116 |
| | Contact angle (°) with liquid oil | 109 | 98 | 92 | 90 | 87 |
| | Water resistance | A | A | A | A | A |
| | Sebum resistance | A | A | A | A | A |

(Note)
"Edetic acid": Ethylenediaminetetraacetic acid
"Carbomer": Carboxyvinyl polymer

TABLE 2

| | Component (% by mass) | Comparative Example 1 | Comparative Example 2 | Comparative Example 3 | Comparative Example 4 | Comparative Example 5 | Comparative Example 6 |
|---|---|---|---|---|---|---|---|
| 1 | Purified water | Balance | Balance | Balance | Balance | Balance | Balance |
| 2 | Edetic acid trisodium | Appropriate amount | Appropriate amount | Appropriate amount | Appropriate amount | Appropriate amount | Appropriate amount |

TABLE 2-continued

| | | Comparative Example | | | | | |
|---|---|---|---|---|---|---|---|
| | Component (% by mass) | 1 | 2 | 3 | 4 | 5 | 6 |
| 3 | Glycerol | 5 | 5 | 5 | 5 | 5 | 5 |
| 4 | Dipropylene glycol | 5 | 5 | 5 | 5 | 5 | 5 |
| 5 | Phenoxyethanol | 0.5 | 0.5 | 0.5 | 0.5 | 0.5 | 0.5 |
| 6 | Carbomer | 0.4 | 0.4 | 0.4 | 0.4 | 0.4 | 0.4 |
| 7 | Ethanol | 15 | 12 | 12 | 12 | 12 | 12 |
| 11 | Polymer of Comp. Synthetic Example 1 | — | 3 | — | — | — | — |
| 12 | Polymer of Synthetic Example 2 | — | — | 3 | — | — | — |
| 13 | Polymer of Comp. Synthetic Example 3 | — | — | — | 3 | — | — |
| 14 | Polymer of Comp. Synthetic Example 4 | — | — | — | — | 3 | — |
| 15 | Vinylpyrrolidone-vinyl acetate copolymer | — | — | — | — | — | 3 |
| Physical property | Contact angle (°) with water | 23 | 56 | 62 | 31 | 41 | 57 |
| | Contact angle (°) with liquid oil | 34 | 50 | 39 | 65 | 59 | 42 |
| | Water resistance | C | C | C | C | C | C |
| | Sebum resistance | C | C | C | C | C | C |

(Note)
"Edetic acid": Ethylenediaminetetraacetic acid
"Carbomer": Carboxyvinyl polymer

TABLE 3

| | | Example | | | | |
|---|---|---|---|---|---|---|
| | Component (% by mass) | 6 | 7 | 8 | 9 | 10 |
| 1 | Purified water | Balance | Balance | Balance | Balance | Balance |
| 2 | Edetic acid trisodium | Appropriate amount | Appropriate amount | Appropriate amount | Appropriate amount | Appropriate amount |
| 3 | Phenoxyethanol | Appropriate amount | Appropriate amount | Appropriate amount | Appropriate amount | Appropriate amount |
| 4 | Glycerol | 5 | 5 | 5 | 5 | 5 |
| 5 | Dipropylene glycol | 5 | 5 | 5 | 5 | 5 |
| 6 | Polyoxyethylene glycerol monostearate | 1.2 | 1.2 | 1.2 | 1.2 | 1.2 |
| 7 | Carbomer | 0.5 | 0.5 | 0.5 | 0.5 | 0.5 |
| 8 | Ethanol | 12 | 12 | 12 | 6 | 5 |
| 9 | Polymer of Synthetic Example 1 | 3 | — | — | 1.5 | 1 |
| 10 | Polymer of Synthetic Example 2 | — | 3 | — | — | — |
| 11 | Polymer of Synthetic Example 3 | — | — | 3 | — | — |
| 17 | Decamethylcyclopentasiloxane | 17 | 17 | 17 | 17 | 17 |
| 18 | 2-Ethylhexyl p-methoxycinnamate | 3 | 3 | 3 | 3 | 3 |
| 19 | Amodimethicone | 2 | 2 | 2 | 2 | 2 |
| 20 | Isostearic acid | 0.5 | 0.5 | 0.5 | 0.5 | 0.5 |
| 21 | Alkyl-modified silicone-treated titanium dioxide | 10 | 10 | 10 | 10 | 10 |
| 22 | Perfume | Appropriate amount | Appropriate amount | Appropriate amount | Appropriate amount | Appropriate amount |
| Physical property | Contact angle (°) with water | 110 | 106 | 100 | 100 | 95 |
| | Contact angle (°) with liquid oil | 88 | 90 | 86 | 74 | 71 |
| | Water resistance | A | A | A | A | A |
| | Sebum resistance | A | A | A | A | A |

(Note)
"Edetic acid": Ethylenediaminetetraacetate
"Carbomer": Carboxyvinyl polymer

TABLE 4

| | | Comparative Example | | | | | |
|---|---|---|---|---|---|---|---|
| | Component (% by mass) | 7 | 8 | 9 | 10 | 11 | 12 |
| 1 | Purified water | Balance | Balance | Balance | Balance | Balance | Balance |
| 2 | Edetic acid trisodium | Appropriate amount | Appropriate amount | Appropriate amount | Appropriate amount | Appropriate amount | Appropriate amount |
| 3 | Phenoxyethanol | Appropriate amount | Appropriate amount | Appropriate amount | Appropriate amount | Appropriate amount | Appropriate amount |
| 4 | Glycerol | 5 | 5 | 5 | 5 | 5 | 5 |
| 5 | Dipropylene glycol | 5 | 5 | 5 | 5 | 5 | 5 |
| 6 | Polyoxyethylene glyceryl monostearate | 1.2 | 1.2 | 1.2 | 1.2 | 1.2 | 1.2 |

TABLE 4-continued

| | Component (% by mass) | Comparative Example | | | | | |
|---|---|---|---|---|---|---|---|
| | | 7 | 8 | 9 | 10 | 11 | 12 |
| 7 | Carbomer | 0.5 | 0.5 | 0.5 | 0.5 | 0.5 | 0.5 |
| 8 | Ethanol | 15 | 12 | 12 | 12 | 12 | 12 |
| 11 | Polymer of Synthetic Example 1 | — | — | — | — | — | — |
| 12 | Polymer of Comp. Synthetic Example 1 | — | 3 | — | — | — | — |
| 13 | Polymer of Comp. Synthetic Example 2 | — | — | 3 | — | — | — |
| 14 | Polymer of Comp. Synthetic Example 3 | — | — | — | 3 | — | — |
| 15 | Polymer of Comp. Synthetic Example 4 | — | — | — | — | 3 | — |
| 16 | Vinylpyrrolidone-vinyl acetate copolymer | — | — | — | — | — | 3 |
| 17 | Decamethylcyclopentasiloxane | 17 | 17 | 17 | 17 | 17 | 17 |
| 18 | 2-Ethylhexyl p-Methoxycinnamate | 3 | 3 | 3 | 3 | 3 | 3 |
| 19 | Amodimethicone | 2 | 2 | 2 | 2 | 2 | 2 |
| 20 | Isostearic acid | 0.5 | 0.5 | 0.5 | 0.5 | 0.5 | 0.5 |
| 21 | Alkyl-modified silicone-treated titanium dioxide | 10 | 10 | 10 | 10 | 10 | 10 |
| 22 | Perfume | Appropriate amount | Appropriate amount | Appropriate amount | Appropriate amount | Appropriate amount | Appropriate amount |
| Physical property | Contact angle (°) with water | 70 | 78 | 75 | 61 | 52 | 40 |
| | Contact angle (°) with liquid oil | 36 | 45 | 43 | 75 | 60 | 63 |
| | Water resistance | C | C | C | C | C | C |
| | Sebum resistance | C | C | C | B | C | C |

(Note)
"Edetic acid": Ethylenediaminetetraacetate
"Carbomer": Carboxyvinyl polymer From the results shown in Tables 1 to 4, it can be seen that the cosmetic obtained in each Example has a very high contact angle with each of water and liquid oil, and that the cosmetic is excellent in water resistance and sebum resistance. To the contrary, it can be seen that the cosmetic obtained in each Comparative Example has a low contact angle with each of water and liquid oil, and that the cosmetic is low in water resistance and sebum resistance.

Next, Formulation Examples of the cosmetic of the present invention will be described below. The present invention is not limited only to those examples.

Formulation Example 1 [Sunscreen Cream]

Sunscreen cream was prepared by mixing the following components with each other. It was confirmed that the resulting sunscreen cream had water repellency and oil repellency, and was excellent in water resistance and sebum resistance.

| (1) | polymer obtained in Synthetic Example 1 | 2 parts by mass |
|---|---|---|
| (2) | ethanol | 8 parts by mass |
| (3) | dimethylpolysiloxane | 5 parts by mass |
| (4) | decamethylcyclopentasiloxane | 25 parts by mass |
| (5) | trimethylsiloxysilicate | 5 parts by mass |
| (6) | polyoxyethylene-methylpolysiloxane copolymer | 2 parts by mass |
| (7) | dipropylenglycol | 5 parts by mass |
| (7) | fine particles of zinc oxide | 15 parts by mass |
| (8) | paraben | appropriate amount |
| (9) | phenoxyethanol | appropriate amount |
| (10) | trisodium ethylenediaminetetraacetate | appropriate amount |
| (11) | 2-ethylhexyl p-methoxycinnamate | 7.5 parts by mass |
| (12) | dimethyl distearyl ammonium hectorite | 0.5 parts by mass |
| (13) | spherical powders of polyalkyl acrylate | 5 parts by mass |
| (14) | perfume | appropriate amount |
| (15) | purified water | balance |

Formulation Example 2 [Sunscreen Emulsion]

Sunscreen emulsion was prepared by mixing the following components with each other so as to have a total amount of 100 parts by mass. It was confirmed that the resulting sunscreen emulsion had water repellency and oil repellency, and that the sunscreen emulsion was excellent in water resistance and sebum resistance.

| (1) | polymer obtained in Synthetic Example 1 | 2 parts by mass |
|---|---|---|
| (2) | ethanol | 8 parts by mass |
| (3) | vaseline | 1 part by mass |
| (4) | dimethylpolysiloxane | 3 parts by mass |
| (5) | methylphenyl polysiloxane | 3 parts by mass |
| (6) | stearyl alcohol | 0.5 parts by mass |
| (7) | glycerol | 7 parts by mass |
| (8) | dipropylenglycol | 3 parts by mass |
| (9) | 1,3-butylene glycol | 7 parts by mass |
| (10) | xylitol | 3 parts by mass |
| (11) | squalane | 1 part by mass |
| (12) | isostearic acid | 0.5 parts by mass |
| (13) | stearic acid | 0.5 parts by mass |
| (14) | polyoxyethylene glyceryl monostearate | 1 part by mass |
| (15) | glyceryl monostearate | 2 parts by mass |
| (16) | potassium hydroxide | 0.05 parts by mass |
| (17) | magnesium L-ascorbyl phosphate | 0.1 parts by mass |
| (18) | tocopherol acetate | 0.1 parts by mass |
| (19) | sodium acetylated hyaluronate | 0.1 parts by mass |
| (20) | trisodium ethylenediaminetetraacetate | 0.05 parts by mass |
| (21) | 4-tert-butyl-4'-methoxydibenzoylmethane | 2 parts by mass |
| (22) | 2-ethylhexyl 4-methoxycinnamate | 5 parts by mass |
| (23) | carboxyvinyl polymer | 0.1 parts by mass |
| (24) | phenoxyethanol | appropriate amount |
| (25) | perfume | appropriate amount |
| (26) | purified water | balance |

Formulation Example 3 [Sunscreen Gel]

Sunscreen gel was prepared by mixing the following components with each other so as to have a total amount of 100 parts by mass. It was confirmed that the resulting sunscreen gel had water repellency and oil repellency, and that the sunscreen gel was excellent in water resistance and sebum resistance.

| (1) | polymer obtained in Synthetic Example 1 | 2 parts by mass |
|---|---|---|
| (2) | ethanol | 15 parts by mass |
| (3) | butanediol | 5 parts by mass |

-continued

| (4) | triethanolamine | 0.1 parts by mass |
|---|---|---|
| (5) | phenoxyethanol | appropriate amount |
| (6) | disodium ethylenediaminetetraacetate | appropriate amount |
| (7) | PEG/PPG-19/19 dimethicone | 4 parts by mass |
| (8) | PEG-60 glyceryl isostearate | 0.1 parts by mass |
| (9) | ethylhexyl methoxycinnamate | 5 parts by mass |
| (10) | octocrylene | 2 parts by mass |
| (11) | bis-ethylhexyloxyphenol methoxyphenyl triazine | 3 parts by mass |
| (12) | xanthan gum | 0.1 parts by mass |
| (13) | copolymer of acrylic acid-alkyl acrylate (the number of carbon atoms of the alkyl group: 10 to 30) | 0.1 parts by mass |
| (14) | carbomer | 0.1 parts by mass |
| (15) | perfume | appropriate amount |
| (16) | tranexamic acid | 2 parts by mass |
| (17) | talc | 3 parts by mass |
| (18) | oxybenzone | 1 part by mass |
| (19) | purified water | balance |

Formulation Example 4 [Mascara]

Mascara was prepared by mixing the following components with each other so as to have a total amount of 100 parts by mass. It was confirmed that the resulting mascara had water repellency and oil repellency, and that the mascara was excellent in water resistance and sebum resistance.

| (1) | polymer obtained in Synthetic Example 1 | 2 parts by mass |
|---|---|---|
| (2) | methyl polysiloxane emulsion | appropriate amount |
| (3) | ethanol | 8 parts by mass |
| (4) | isopropanol | 3 parts by mass |
| (5) | glycerol | 3 parts by mass |
| (6) | 1,3-butylene glycol | 5 parts by mass |
| (7) | silicic anhydride | 1 part by mass |
| (8) | red iron oxide coated titanated mica (pearlescent agent) | 9 parts by mass |
| (9) | strong aqueous ammonia | 0.1 parts by mass |
| (10) | sodium metaphosphate | 0.1 parts by mass |
| (11) | hydrolyzed wheat protein | 0.1 parts by mass |
| (12) | p-hydroxybenzoate | appropriate amount |
| (13) | sodium dehydroacetate | appropriate amount |
| (14) | black iron oxide(pigment) | 1 part by mass |
| (15) | xanthan gum | 1 part by mass |
| (16) | aluminum magnesium silicate | 2 parts by mass |
| (17) | sodium carboxymethylcellulose | 1 part by mass |
| (18) | alkyl acrylate-based resin emulsion | 10 parts by mass |
| (19) | purified water | balance |

Formulation Example 5 [Foundation]

Foundation was prepared by mixing the following components with each other so as to have a total amount of 100 parts by mass. It was confirmed that the resulting foundation had water repellency and oil repellency, and that the foundation was excellent in water resistance and sebum resistance

| (1) | polymer obtained in Synthetic Example 1 | 2 parts by mass |
|---|---|---|
| (2) | ethanol | 8 parts by mass |
| (3) | dimethylpolysiloxane | 8 parts by mass |
| (4) | behenyl alcohol | 0.5 parts by mass |
| (5) | batyl alcohol | 0.5 parts by mass |
| (6) | 1,3-butylene glycol | 5 parts by mass |
| (7) | macadamia nut oil | 0.1 parts by mass |
| (8) | isostearic acid | 1.5 parts by mass |
| (9) | stearic acid | 1 part by mass |
| (10) | behenic acid | 0.5 parts by mass |
| (11) | cetyl 2-ethylhexanoate | 5 parts by mass |
| (12) | polyoxyethylene glyceryl monostearate | 1 part by mass |
| (13) | Self-emulsifying glyceryl monostearate | 1 part by mass |
| (14) | yellow iron oxide coated titanated mica | 2 parts by mass |
| (15) | titanium oxide | 4 parts by mass |
| (16) | talc | 0.5 parts by mass |
| (17) | kaolin | 3 parts by mass |
| (18) | synthetic phlogopite | 0.1 parts by mass |
| (19) | cross-linked type silicone powder | 0.1 parts by mass |
| (20) | silicic anhydride | 5 parts by mass |
| (21) | potassium hydroxide | 0.2 parts by mass |
| (22) | triethanolamine | 0.8 parts by mass |
| (23) | dl-α-tocopherol acetate | 0.1 parts by mass |
| (24) | sodium hyaluronate | 0.1 parts by mass |
| (25) | p-hydroxybenzoate | appropriate amount |
| (26) | 2-ethylhexyl 4-methoxycinnamate | 1 part by mass |
| (27) | red iron oxide | appropriate amount |
| (28) | yellow iron oxide | appropriate amount |
| (29) | black iron oxide | appropriate amount |
| (30) | xanthan gum | 0.1 parts by mass |
| (31) | bentonite | 1 part by mass |
| (32) | sodium carboxymethylcellulose | 0.1 parts by mass |
| (33) | perfume | appropriate amount |
| (34) | purified water | balance |

Formulation Example 6 [Oil-in-Water Emulsion Foundation]

Oil-in-water emulsion foundation was prepared by mixing the following components with each other so as to have a total amount of 100 parts by mass. It was confirmed that the resulting oil-in-water emulsion foundation had water repellency and oil repellency, and that the oil-in-water emulsion was excellent in water resistance and sebum resistance.

| (1) | polymer obtained in Synthetic Example 1 | 2 parts by mass |
|---|---|---|
| (2) | alkyl-modified silicone resin-coated titanium oxide | 9 parts by mass |
| (3) | alkyl-modified silicone resin-coated ultrafine particle titanium oxide | 5 parts by mass |
| (4) | alkyl-modified silicone resin coated iron oxide (red) | 0.5 parts by mass |
| (5) | alkyl-modified silicone resin coated iron oxide (yellow) | 1.5 parts by mass |
| (6) | alkyl-modified silicone resin coated iron oxide (black) | 0.2 parts by mass |
| (7) | polyoxyalkylene-modified organopolysiloxane | 0.5 parts by mass |
| (8) | decamethylcyclopentasiloxane | 5 parts by mass |
| (9) | octyl p-methoxycinnamate | 5 parts by mass |
| (10) | acrylic silicone | 4 parts by mass |
| (11) | PEG-100 hydrogenated castor oil | 2 parts by mass |
| (12) | dynamite glycerol | 6 parts by mass |
| (13) | xanthan gum | appropriate amount |
| (14) | carboxymethyl cellulose | appropriate amount |
| (15) | sodium acryloyldimethyltaurine/hydroxyethyl acrylate copolymer | 0.5 parts by mass |
| (16) | ethanol | 8 parts by mass |
| (17) | ion exchange water | balance |

Formulation Example 7 [Foundation Primer]

Foundation primer was prepared by mixing the following components with each other so as to have a total amount of 100 parts by mass. It was confirmed that the resulting foundation primer had water repellency and oil repellency, and that the foundation primer was excellent in water resistance

| | | |
|---|---|---|
| (1) | polymer obtained in Synthetic Example 1 | 2 parts by mass |
| (2) | ethanol | 8 parts by mass |
| (3) | α-olefin oligomer | 10 parts by mass |
| (4) | dimethylpolysiloxane | 5 parts by mass |
| (5) | behenyl alcohol | 0.5 parts by mass |
| (6) | batyl alcohol | 0.5 parts by mass |
| (7) | 1,3-butylene glycol | 5 parts by mass |
| (8) | isostearic acid | 1 part by mass |
| (9) | stearic acid | 1 part by mass |
| (10) | behenic acid | 1 part by mass |
| (11) | cetyl 2-ethylhexanoate | 2 parts by mass |
| (12) | di(phytosteryl/octyldodecyl)-N-lauroyl-L-glutamate | 0.1 parts by mass |
| (13) | polyoxyethylene glyceryl monostearate | 2 parts by mass |
| (14) | self-emulsifying glyceryl monostearate | 0.5 parts by mass |
| (15) | talc | 0.5 parts by mass |
| (16) | titanated mica | 0.5 parts by mass |
| (17) | black iron oxide-coated titanated mica | 0.1 parts by mass |
| (18) | potassium hydroxide | 0.2 parts by mass |
| (19) | sodium metaphosphate | 0.5 parts by mass |
| (20) | tocopherol acetate | 0.1 parts by mass |
| (21) | p-hydroxybenzoate | appropriate amount |
| (22) | 2-ethylhexyl 4-methoxycinnamate | 3 parts by mass |
| (23) | colored pigment | appropriate amount |
| (24) | xanthan gum | 0.1 parts by mass |
| (25) | bentonite | 1 part by mass |
| (26) | sodium carboxymethylcellulose | 0.1 parts by mass |
| (27) | spherical powder of alkyl polyacrylate | 0.1 parts by mass |
| (28) | spherical silicic anhydride | 5 parts by mass |
| (29) | titanium oxide | 5 parts by mass |
| (30) | perfume | appropriate amount |
| (31) | purified water | balance |

Formulation Example 8 [Hair Spray]

A stock solution of hair spray was prepared by mixing the following components with each other so as to have a total amount of 100 parts by mass. An aerosol product was prepared by filling an aerosol container with 92 parts by mass of the resulting stock solution of the hair spray and 8 parts by mass of a propellant (liquefied petroleum gas) so as to have a filling pressure of 0.43 MPa. The hair spray was ejected from the aerosol product. As a result, it was confirmed that the hair spray had water repellency and oil repellency, and that the hair spray was excellent in water resistance and sebum resistance.

| | | |
|---|---|---|
| (1) | polymer obtained in Synthetic Example 1 | 2 parts by mass |
| (2) | ethanol | 8 parts by mass |
| (3) | zwitterionic polymer [manufactured by Mitsubishi Chemical Corporation, trade name: YUKAFORMER SM] | 12 parts by mass |
| (4) | vinylpyrrolidone-N,N-dimethylaminoethyl methacrylate copolymer | 5 parts by mass |
| (5) | 2-alkyl-N-carboxymethyl-N-hydroxyethylimidazolinium betaine | 1 part by mass |
| (6) | polyoxyethylene hydrogenated castor oil (number of moles of oxyethylene group added: 60 mol) | 0.5 parts by mass |
| (7) | alkyltrimethylammonium chloride | 0.2 parts by mass |
| (8) | p-methoxybenzoate | appropriate amount |
| (9) | perfume | appropriate amount |
| (10) | purified water | balance |

Formulation Example 9 [Hair Wax]

Hair wax was prepared by mixing the following components with each other so as to have a total amount of 100 parts by mass. It was confirmed that the resulting hair wax had water repellency and oil repellency, and that the hair wax was excellent in water resistance and sebum resistance.

| | | |
|---|---|---|
| (1) | polymer obtained in Synthetic Example 1 | 2 parts by mass |
| (2) | ethanol | 8 parts by mass |
| (3) | polyethylene glycol (average molecular weight: 400) | 3 parts by mass |
| (4) | cetyl 2-ethylhexanoate | 0.5 parts by mass |
| (5) | polyoxyethylene hydrogenated castor oil | 0.15 parts by mass |
| (6) | sodium hydroxide | 0.1 parts by mass |
| (7) | p-hydroxybenzoate | appropriate amount |
| (8) | trisodium ethylenediaminetetraacetate | appropriate amount |
| (9) | curdlan | 0.6 parts by mass |
| (10) | xanthan gum | 0.1 parts by mass |
| (11) | betaine polymer [manufactured by Mitsubishi Chemical Corporation, trade name: YUKAFORMER 301] | 10 parts by mass |
| (12) | carboxyvinyl polymer | 0.5 parts by mass |
| (13) | perfume | appropriate amount |
| (14) | purified water | balance |

Formulation Example 10 [Overcoating Agent]

An overcoating agent was prepared by mixing the following components with each other so as to have a total amount of 100 parts by mass. It was confirmed that the resulting overcoating agent had water repellency and oil repellency, and that the overcoating agent was excellent in water resistance and sebum resistance.

| | | |
|---|---|---|
| (1) | trisodium ethylenediaminetetraacetate | 0.1 parts by mass |
| (2) | glycerol | 5 parts by mass |
| (3) | dipropylenglycol | 5 parts by mass |
| (4) | phenoxyethanol | 0.5 parts by mass |
| (5) | (dimethylacrylamide/sodium acryloyldimethyltaurine) crosspolymer | 0.4 parts by mass |
| (6) | ethanol | 8 parts by mass |
| (7) | polymer obtained in Synthetic Example 1 | 2 parts by mass |
| (8) | perfume | appropriate amount |
| (9) | purified water | balance |

The invention claimed is:

1. A cosmetic comprising a polymer formed by a polymerization of a monomer component comprising:

(A) a fluorine atom-containing monomer represented by the formula (I):

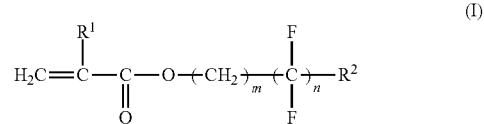

(I)

wherein $R^1$ is hydrogen atom or methyl group, $R^2$ is hydrogen atom or fluorine atom, m is 0 or an integer of 1 to 4, and n is an integer of 1 to 12;

(B) a betaine monomer represented by the formula (II):

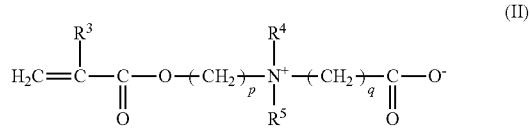

(II)

wherein $R^3$ is hydrogen atom or methyl group, each of $R^4$ and $R^5$ is independently hydrogen atom or an alkyl group having 1 to 4 carbon atoms, p is an integer of 1 to 4, and q is an integer of 1 to 4; and (C) an alkyl (meth)acrylate represented by the formula (III):

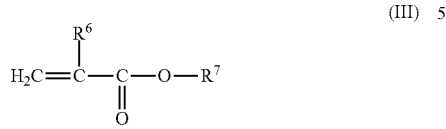

(III)

wherein $R^6$ is hydrogen atom or methyl group, and $R^7$ is an alkyl group having 8 to 22 carbon atoms.

2. The cosmetic according to claim 1, wherein the monomer component further comprises a monomer having a sulfonic acid group or a sulfonate group.

3. The cosmetic according to claim 1, wherein the monomer component further comprises a cross-linking agent represented by the formula (IV):

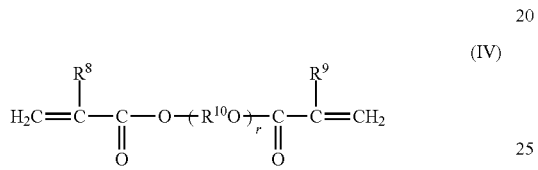

(IV)

wherein each of $R^8$ and $R^9$ is independently hydrogen atom or methyl group, $R^{10}$ is an alkylene group having 2 or 3 carbon atoms, and r is an integer of 1 to 40.

* * * * *